(12) United States Patent
Hamada et al.

(10) Patent No.: US 10,717,693 B2
(45) Date of Patent: Jul. 21, 2020

(54) METHOD FOR PRODUCING DIOL

(71) Applicant: DAIKIN INDUSTRIES, LTD., Osaka-Shi, Osaka (JP)

(72) Inventors: Tomohito Hamada, Osaka (JP); Michiaki Okada, Osaka (JP); Akinori Yamamoto, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/777,494

(22) PCT Filed: Nov. 22, 2016

(86) PCT No.: PCT/JP2016/084626
§ 371 (c)(1),
(2) Date: May 18, 2018

(87) PCT Pub. No.: WO2017/090621
PCT Pub. Date: Jun. 1, 2017

(65) Prior Publication Data
US 2018/0327342 A1  Nov. 15, 2018

(30) Foreign Application Priority Data

Nov. 24, 2015 (JP) .................. 2015-229019

(51) Int. Cl.
*C07C 29/48* (2006.01)
*C07C 31/42* (2006.01)
*C07C 253/30* (2006.01)
*C07C 255/12* (2006.01)
*B01J 27/13* (2006.01)
*C07B 61/00* (2006.01)

(52) U.S. Cl.
CPC .............. *C07C 29/48* (2013.01); *B01J 27/13* (2013.01); *C07C 31/42* (2013.01); *C07C 253/30* (2013.01); *C07C 255/12* (2013.01); *C07B 61/00* (2013.01)

(58) Field of Classification Search
CPC ........... C07C 29/48; C07C 31/42; B01J 27/13
USPC ........................................................ 568/842
See application file for complete search history.

(56) References Cited

U.S. PATENT DOCUMENTS 6,825,377 B1  11/2004  Beller et al.

FOREIGN PATENT DOCUMENTS

| JP | 2002-543051 A | 12/2002 |
| JP | 02543051 A | * 12/2002 |
| JP | 2010-527748 A | 8/2010 |
| WO | 2008/141027 A2 | 11/2008 |

OTHER PUBLICATIONS

Shing K.M. Tony, et al., RutheniumCatalyzed cis-Dihydroxylation of Alkenes: Scope and Limitations, Chem. Eur. J., 1996.*
Clifford A.F., The Electronegativity of Groups, J. Phys. Chem., 1959, vol. 63, No., pp. 1227-1231, table II.*
Tony K. M. Shing, et al., "Ruthenium-Catalyzed cis-Dihydroxylation of Alkenes: Scope and Limitations", Chem. Eur. J., 1996, pp. 50-57, vol. 2, No. 1.
A. F. Clifford, "The Electronegativity of Groups", J. Phys. Chem, 1959, pp. 1227-1231, vol. 63, No. 8.
James E. Huheey, "The Electronegativity of Groups", J. Phys. Chem., 1965, pp. 3284-3291, vol. 69, No. 10.
James E. Huheey, "The Electronegativity of Multiply Bonded Groups", J. Phys. Chem., 1966, pp. 2086-2092, vol. 70, No. 7.
John Mullay, "Calculation of Group Electronegativity", J. Am. Chem. Soc., 1985, pp. 7271-7275, vol. 107, No. 25.
Bernd Plietker, et al., An Improved Protocol for the $RuO_4$-Catalyzed Dihydroxylation of Olefins, Org. Lett., 2003, pp. 3353-3356, vol. 5, No. 18.
International Search Report for PCT/JP2016/084626 dated Jan. 10, 2017 [PCT/ISA/210].
International Preliminary Report on Patentability with translation of Written Opinion dated May 29, 2018, in counterpart International Application No. PCT/JP2016/084626.
Megumi Fujita et al: "Iron-Catalyzed Olefin cis-Dihydroxylation by $H_2O_2$ : Electrophilic versus Nucleophilic Mechanisms", Journal of the American Chemical Society, vol. 125, No. 33, Aug. 1, 2003 (Aug. 1, 2003), pp. 9912-9913, XP55576551, ISSN: 0002-7863, DOI: 10.1021/ja029863d.
Becker H et al: "A New Ligand Class for the Asymmetric Dihydroxylation of Olefins", Angewandte Chemie, International Edition, vol. 35, No. 4, Mar. 1, 1996 (Mar. 1, 1996), pp. 448-451, XP002068086, ISSN: 1433-7851, DOI: 10.1002/ANIE.199604481.
Extended European Search Report for counterpart EP 16868564.2 dated Jul. 4, 2019.
Bernd Plietker et al., "The acid accelerated ruthenium-catalysed dihydroxylation. Scope and limitations", Organic & Biomolecular Chemistry, vol. 2, No. 8, pp. 1116-1124, Jan. 1, 2004, XP55576588, 9 pages total.
Partial Supplementary European Search Report dated Apr. 9, 2019 issued by the European Patent Office in counterpart application No. 16868564.2.

(Continued)

*Primary Examiner* — Deborah D Carr
(74) *Attorney, Agent, or Firm* — Sughrue Mion, PLLC

(57) ABSTRACT

The present invention provides a method for producing a diol having a specific structure in high yields while keeping high selectivity. Provided is a method for producing a diol having a specific structure by oxidizing an olefin having a specific structure in the presence of a ruthenium compound.

11 Claims, No Drawings

(56) References Cited

OTHER PUBLICATIONS

Herrmann et al., "Multiple Bonds between Atoms of Main Group Elements and Transition Metals, CVIII [1],—Stoichiometric and Catalytic Oxidation of Electron-poor Olefins with Osmium Tetraoxide: A Novel Oxidation Method for Fluoroolefins", Chem. Ber. vol. 126, pp. 31-37, 1993, 11 pages total.

* cited by examiner

METHOD FOR PRODUCING DIOL

CROSS REFERENCE TO RELATED APPLICATIONS

This application is a National Stage of International Application No. PCT/JP2016/084626, filed on Nov. 22, 2016, which claims priority from Japanese Patent Application No. 2015-229019, filed on Nov. 24, 2015.

TECHNICAL FIELD

The present invention relates to a method for producing a diol. The present invention also relates to a composition containing a diol.

BACKGROUND ART

Patent Literature 1 reports conversion of an olefin oxide to a 1,2-diol or a 1,2-diol ether by reacting an olefin oxide with water appropriately using an acidic catalyst or a basic catalyst.

Non-patent Literature 1 reports production of a diol by oxidizing an olefin such as methyl cinnamate using ruthenium trichloride and an acid in a solvent mixture of ethyl acetate, acetonitrile, and water.

CITATION LIST

Patent Literature

Patent Literature 1: JP 2010-527748 T

Non-Patent Literature

Non-patent Literature 1: B. Plietker, M. Niggemann, "An Improved Protocol for the RuO$_4$—Catalyzed Dihydroxylation of Olefins", Org. Lett., 2003, 3353-3356.

SUMMARY OF INVENTION

Technical Problem

The present invention aims to provide a method for producing a diol having a specific structure in high yields while keeping high selectivity.

Solution to Problem

The present invention relates to a method for producing a diol, including
oxidizing an olefin represented by Formula (1):

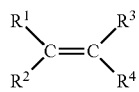

wherein $R^1$ is a group having an electronegativity of 3.0 to 5.0; and $R^2$ to $R^4$ are each independently a hydrogen atom, a cyano group, or an optionally substituted alkyl group, in the presence of a ruthenium compound to produce a diol represented by Formula (2):

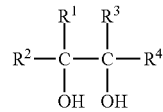

wherein $R^1$ to $R^4$ are as defined above (hereinafter also referred to as "the first production method of the present invention" or "the first production method").

In the first production method of the present invention, preferably one of $R^2$ to $R^4$ is a hydrogen atom.

In the first production method of the present invention, preferably two of $R^2$ to $R^4$ are hydrogen atoms.

In the first production method of the present invention, preferably $R^2$ to $R^4$ are all hydrogen atoms.

In the first production method of the present invention, the ruthenium compound can be collected after the oxidization of the olefin.

The present invention also relates to a method for producing a diol, including
oxidizing an olefin represented by Formula (3):

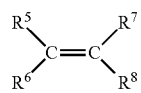

wherein $R^5$ is a cyano group or an optionally substituted alkyl group; and $R^6$ to $R^8$ are each independently a hydrogen atom, a cyano group, or an optionally substituted alkyl group, in the presence of a ruthenium compound to produce a diol represented by Formula (4):

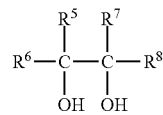

wherein $R^5$ to $R^8$ are as defined above (hereinafter also referred to as "the second production method of the present invention" or "the second production method").

In the second production method of the present invention, preferably one of $R^6$ to $R^8$ is a hydrogen atom.

In the second production method of the present invention, preferably two of $R^6$ to $R^8$ are hydrogen atoms.

In the second production method of the present invention, preferably $R^6$ to $R^8$ are all hydrogen atoms.

In the second production method of the present invention, the ruthenium compound can be collected after the oxidization of the olefin.

The present invention also relates to a composition containing:
a diol represented by Formula (4):

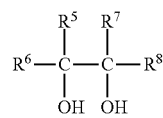

wherein $R^5$ is a cyano group or an optionally substituted alkyl group; and $R^6$ to $R^8$ are each independently a hydrogen atom, a cyano group, or an optionally substituted alkyl group, and an acid compound represented by Formula (5):

$$R^5—COOH$$

wherein $R^5$ is as defined above,
the composition containing the acid compound in an amount of 1,000 to 10,000 ppm.

Advantageous Effects of Invention

The first production method of the present invention with the above-described feature enables production of diols having the specific structure in high yields while keeping high selectivity.

The second production method of the present invention with the above-described feature enables production of diols having the specific structure in high yields while keeping high selectivity.

The composition of the present invention having the above-described structure exhibits an advantageous effect; specifically, it is readily extracted in a separation operation. Thus, the composition can suitably be used for obtaining very pure target objects.

DESCRIPTION OF EMBODIMENTS

The present invention is specifically described below.
The first production method is a method for producing a diol represented by Formula (2) by oxidizing an olefin represented by Formula (1) in the presence of a ruthenium compound.
The olefin is represented by Formula (1):

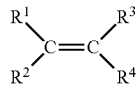

wherein $R^1$ is a group having an electronegativity of 3.0 to 5.0; and $R^2$ to $R^4$ are each independently a hydrogen atom, a cyano group, or an optionally substituted alkyl group.

The electronegativity is preferably 3.3 or higher but preferably 4.6 or lower.

The electronegativity can be determined by the method described in J. Phys. Chem., 1965, 69, 3284-3291.

$R^1$ is preferably a cyano group or a fluorine-containing alkyl group, more preferably a fluorine-containing alkyl group. The fluorine-containing alkyl group preferably has one to 10 carbon atom(s), more preferably one to five carbon atom(s), still more preferably one to three carbon atom(s), particularly preferably one or two carbon atom(s). $R^1$ is furthermore preferably at least one selected from the group consisting of —$CF_3$, —CN, —$C_2F_5$, —$CH_2CF_3$, —$CH_2CF_3$, —$CH_2CF_2H$, —$CH_2CFH_2$, —$CH(CF_3)_2$, and —$CF(CF_3)_2$.

For reference, the electronegativity of several groups is as follows.
—$CF_3$: 3.46
—$CF_2CF_3$: 3.4
—$CF(CF_3)_2$: 3.38
—CN: 3.84
—$CH_3$: 2.27

Examples of the substituent include an aryl group, an alkoxy group, a halogen atom, a cyano group, an ether group, an ester group, and an amide group, all of which may contain a heteroatom. Preferred of these is a cyano group, an aryl group, a fluorine atom, or a chlorine atom; more preferred is a cyano group or a fluorine atom; and still more preferred is a fluorine atom.

$R^2$ to $R^4$ are each preferably a hydrogen atom, a cyano group, or a fluorine-containing alkyl group, more preferably a hydrogen atom or a fluorine-containing alkyl group. The fluorine-containing alkyl group preferably has one to 10 carbon atom(s), more preferably one to five carbon atom(s), still more preferably one to three carbon atom(s), particularly preferably one or two carbon atom(s).

Preferably, one of $R^2$ to $R^4$ is a hydrogen atom. More preferably, two of $R^2$ to $R^4$ are hydrogen atoms. Still more preferably, $R^2$ to $R^4$ are all hydrogen atoms.

The diol is represented by Formula (2):

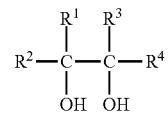

wherein $R^1$ to $R^4$ are as defined above.
Specific examples of the diol include $CF_3$—CHOH—$CH_2OH$, $CF_2H$—CHOH—$CH_2OH$, $CFH_2$—CHOH—$CH_2OH$, $CF_3CF_2$—CHOH—$CH_2OH$, $CF_2HCH_2$—CHOH—$CH_2OH$, $CFH_2CH_2$—CHOH—$CH_2OH$, NC—CHOH—$CH_2OH$, $CH_2OH$—CHOH—$CH_2CN$, $CF_3CH_2$—CHOH—$CH_2OH$, and $(CF_3)_2CF$—CHOH—$CH_2OH$.

The first production method is particularly suitable for producing a diol such as $CF_3$—CHOH—$CH_2OH$, NC—CHOH—$CH_2OH$, $CF_3CF_2$—CHOH—$CH_2OH$, $CF_3CH_2$—CHOH—$CH_2OH$, or $(CF_3)_2CF$—CHOH—$CH_2OH$.

The second production method is a method for producing a diol represented by Formula (4) by oxidizing an olefin represented by Formula (3) in the presence of a ruthenium compound.
The olefin is represented by Formula (3):

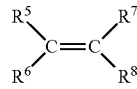

wherein $R^5$ is a cyano group or an optionally substituted alkyl group; and $R^6$ to $R^8$ are each independently a hydrogen atom, a cyano group, or an optionally substituted alkyl group.

$R^5$ is preferably a fluorine-containing alkyl group. The fluorine-containing alkyl group preferably has not more than 10 carbon atoms, more preferably not more than five carbon atoms, still more preferably not more than three carbon atoms, furthermore preferably not more than two carbon atoms. It may have one or more carbon atoms.

$R^5$ may be a linear or branched fluorine-containing alkyl group.

In particular, for production in high yields while keeping high selectivity, $R^5$ is more preferably at least one selected from the group consisting of —$CF_3$, —$CF_2H$, —$CFH_2$, —$CH_2CF_3$, —$CF_2CF_3$, —$CH(CF_3)_2$, —$CF(CF_3)_2$, —$CH_2C_2F_5$, —$CF_2CF_2H$, —$CF_2CFH_2$, —$CFHCF_3$, —$CFHCF_2H$, —$CFHCFH_2$, —$CH_2CF_2CF_3$, —$CH_2CF_2CF_2H$, and —$CF_2CF_2CF_3$, still more preferably —$CF_3$.

Examples of the substituent include an aryl group, an alkoxy group, a halogen atom, a cyano group, an ether group, an ester group, and an amide group, all of which may contain a heteroatom. Preferred of these is a cyano group, an aryl group, a fluorine atom, or a chlorine atom; more preferred is a cyano group or a fluorine atom; still more preferred is a fluorine atom.

$R^6$ to $R^8$ are each preferably a hydrogen atom, a cyano group, or a fluorine-containing alkyl group, more preferably a hydrogen atom or a fluorine-containing alkyl group. The fluorine-containing alkyl group preferably has one to 10 carbon atom(s), more preferably one to five carbon atom(s), still more preferably one to three carbon atom(s), particularly preferably one or two carbon atom(s).

Preferably, one of $R^6$ to $R^8$ is a hydrogen atom. More preferably, two of $R^6$ to $R^8$ are hydrogen atoms. Still more preferably, $R^6$ to $R^8$ are all hydrogen atoms.

The diol is represented by Formula (4):

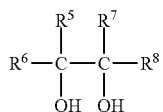

wherein $R^5$ to $R^8$ are as defined above.

Specific examples of the diol include $CF_3$—CHOH—$CH_2OH$, $CF_2H$—CHOH—$CH_2OH$, $CFH_2$—CHOH—$CH_2OH$, $CF_3CF_2$—CHOH—$CH_2OH$, $CF_2HCH_2$—CHOH—$CH_2OH$, $CFH_2CH_2$—CHOH—$CH_2OH$, NC—CHOH—$CH_2OH$, $CH_2OH$—CHOH—$CH_2CN$, $CF_3CH_2$—CHOH—$CH_2OH$, $(CF_3)_2CF$—CHOH—$CH_2OH$, $CF_3$—CHOH—CH(OH) $CF_3$, and $CF_3$—CHOH—CH(OH) $CH_3$.

The second production method is particularly suitable for producing a diol such as $CF_3$—CHOH—$CH_2OH$, $CF_3CF_2$—CHOH—$CH_2OH$, $CF_3CH_2$—CHOH—$CH_2OH$, $(CF_3)_2CF$—CHOH—$CH_2OH$, $CF_3$—CHOH—CH(OH) $CF_3$, or $CF_3$—CHOH—CH(OH)$CH_3$.

Ruthenium compounds are potent oxidizing agents known to oxidize alkenes to ketones or carboxylic acids. They are also known to oxidize diols to carboxylic acids. It is thus a common belief that ruthenium trichloride should not be used in the production of diols while seeking high selectivity. The present inventors intensively studied methods for producing diols having specific structures. As a result, they have found, contrary to expectations, that oxidization of specific olefins using ruthenium compounds can suppress oxidization to ketones or carboxylic acids, whereby diols can be produced in high yields. Based on the finding, the present invention was completed.

Examples of the ruthenium compound include bis(cyclopentadienyl)ruthenium(0), bis(ethylcyclopentadienyl)ruthenium(II), carbonylchlorohydridotris(triphenylphosphine)ruthenium(II), carbonyl(dihydrido)tris(triphenylphosphine)ruthenium(II), chloro(1,5-cyclooctadiene)(pentamethylcyclopentadienyl)ruthenium(II), chloro(cyclopentadienyl)bis(triphenylphosphine)ruthenium(II), dichloro(benzene)ruthenium(II) dimer, dichloro(p-cymene)ruthenium(II) dimer, dichloro(p-cymene)tricyclohexyl phosphine ruthenium(II), dichloro(carbonyl bis(triphenylphosphine)ruthenium(II), dichlorotris(triphenylphosphine) ruthenium(II), ruthenium(III) acetylacetonate, ruthenium (III) chloride, ruthenium(III) iodide, ruthenium(II) oxide, and ruthenium(IV) oxide. Ruthenium(III) chloride, ruthenium(II) oxide, and ruthenium (IV) oxide are preferred, and ruthenium(III) chloride is more preferred.

The amount of the ruthenium compound may be any appropriate amount causing conversion to the diol; for example, usually 0.00001 to 2.0 mol, preferably 0.0001 to 1 mol, still more preferably 0.001 to 0.1 mol per mol of the olefin.

The oxidization is performed at preferably −50° C. to 50° C., more preferably −40° C. to 40° C., still more preferably −30° C. to 30° C., particularly preferably −20° C. to 20° C., most preferably −10° C. to 10° C.

The duration of the oxidization is not particularly limited, but is usually 0.1 to 120 minutes, preferably 1 to 20 minutes.

Changes may occur in the valence of the ruthenium in the ruthenium compound during the reaction. In the case where the ruthenium is reduced by oxidization of the olefin so that the oxidization valence of the ruthenium is reduced, the oxidization valence of the ruthenium in the ruthenium compound can be returned to the original valence by use of an oxidizing agent capable of oxidizing the ruthenium compound or by electrolysis of the ruthenium compound. The amount of the ruthenium compound to be used can be reduced by returning the oxidization valence of the ruthenium to the original valence.

In order to reduce the amount of the ruthenium compound, another oxidizing agent which is different from the ruthenium compound may be used in the diol-producing process. Any oxidizing agent other than the ruthenium compound may be used, and examples thereof include oxidizing agents (reoxidizing agents) capable of oxidizing the ruthenium compound and oxidizing agents capable of oxidizing the olefin.

In the case of using the oxidizing agent which is different from the ruthenium compound, the amount of the ruthenium compound is preferably 0.0001 to 1 mol, more preferably 0.001 to 0.1 mol.

In the case of not using the oxidizing agent which is different from the ruthenium compound, the amount of the ruthenium compound is preferably more than 1 mol but not more than 2 mol.

Preferred examples of the oxidizing agent which is different from the ruthenium compound include salts of perhalogen acids, salts of halogen acids, salts of halous acids, salts of hypohalous acids, hydrogen peroxide, ozone, salts of permanganic acid, salts of chromic acids, and salts of dichromic acids. More preferred are salts of perhalogen acids, for example, salts of periodic acids such as sodium periodate and potassium (meta)periodate. Also preferred are salts of hypohalous acids such as sodium hypochlorite.

The amount of the oxidizing agent which is different from the ruthenium compound may be any appropriate amount causing conversion to the diol; for example, usually, 0.1 to 5.0 mol, preferably 0.5 to 2.0 mol, more preferably 1.0 to 1.5 mol per mol of the olefin. Too small an amount of the oxidizing agent may slow down the conversion to the diol. Too large an amount of the oxidizing agent may promote oxidative cleavage, whereby the yield of the diol may tend to be reduced.

Preferably, the oxidization proceeds in a reaction solvent. Examples of the reaction solvent include water and organic solvents which are not affected by the oxidization.

Examples of the organic solvent include tetrahydrofuran (THF), diethylether, dichloromethane, dichloroethane, dimethylformamide, dimethylacetamide, N-methylpyrrolidone, dimethylimidazolidinone, dimethylsulfoxide (DMSO), chloroform, carbon tetrachloride, acetonitrile, propionitrile, adiponitrile, ethyl acetate, propyl acetate, isopropyl acetate, butyl acetate, methyl propionate, ethyl propionate, propyl propionate, isopropyl propionate, and butyl propionate. Preferred of these are THF, dichloromethane, carbon tetrachloride, acetonitrile, and ethyl acetate.

In the case of using a reaction solvent, the amount thereof is usually within the range of 0.01 to 10 times, preferably 0.1 to 2 times the weight of the olefin.

Water is preferably used as a reaction solvent for the oxidization. Namely, in preferred embodiments of the first and second production methods, the olefin is oxidized in the presence of water and a ruthenium compound.

The reaction solvent may include a water-soluble solvent as well as water. The volume ratio of water and a water-soluble solvent is preferably 10:90 to 90:10, more preferably 20:80 to 80:20, still more preferably 30:70 to 70:30.

The reaction solvent may include a hydrophobic solvent as well as water. The volume ratio of water and a hydrophobic solvent is preferably 10:90 to 90:10, more preferably 20:80 to 80:20, still more preferably 30:70 to 70:30.

Preferably, the oxidization proceeds in a two-phase reaction solvent consisting of an aqueous phase and an oil phase (e.g. the above organic solvent). The reaction will be facilitated when performed in a two-phase reaction solvent. The volume ratio of the aqueous phase and the oil phase is preferably 1:1000 to 1000:1, more preferably 1:500 to 500:1, still more preferably 1:100 to 100:1, furthermore preferably 1:50 to 50:1, particularly preferably 1:10 to 10:1, although not particularly limited thereto.

In the oxidization in a two-phase system consisting of an aqueous phase and an oil phase (e.g. the above organic solvent), phase-transfer catalysts may be used. Examples include crown ethers such as 18-crown-6, 15-crown-5, and 12-crown-4, and quaternary ammonium salts such as tetrabutylammonium fluoride, tetrabutylammonium chloride, tetrabutylammonium bromide, and tetrabutylammonium iodide.

For higher selectivity, the oxidization may be performed in the presence of an acid. Examples of the acid include acetic acid, trifluoroacetic acid, sulfuric acid, hydrochloric acid, methanesulfonic acid, p-toluene sulfonic acid, and nitric acid. Two or more of these acids may be used in admixture. In particular, sulfuric acid is preferred, and it may be concentrated sulfuric acid.

The first and second production methods each may further include distillation of the diol produced by the oxidization.

In the first and second production methods, the ruthenium compound may be collected after the oxidization of the olefin. The collected ruthenium compound can be reused for oxidization of the olefin. For example, the collection can be performed by separating the ruthenium compound from the diol by any technique, subjecting a composition containing the ruthenium compound and the optionally added reaction solvent to filtration to collect the ruthenium compound as filtrate, followed by washing and drying as needed, and activating the ruthenium compound.

The composition of the present invention includes:
a diol represented by Formula (4):

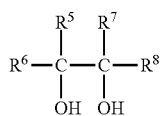

wherein $R^5$ is a cyano group or an optionally substituted alkyl group; and $R^6$ to $R^8$ are each independently a hydrogen atom, a cyano group, or an optionally substituted alkyl group, and an acid compound represented by Formula (5):

$R^5$—COOH wherein $R^5$ is as defined above, the composition containing the acid compound in an amount of 1,000 to 10,000 ppm.

$R^5$ to $R^8$ are as described above concerning the second production method.

In the composition, the proportion of the diol represented by Formula (4) is preferably 30 to 99.99% by mass, more preferably 50 to 99.95% by mass, still more preferably 80 to 99.9% by mass.

The amount of the acid compound is preferably 2,000 ppm or more.

The amount of the acid compound can be measured by $^{19}$F-NMR or $^1$H-NMR.

EXAMPLES

The present invention will be specifically described below with reference to, but not limited to, examples.

Example 1

Sodium periodate (22.5 g, 105 mmol) and water (30 mL) were stirred at 0° C. to 5° C., and ruthenium(III) chloride (71.5 mg, 0.35 mmol), ethyl acetate (100 mL), and acetonitrile (100 mL) were added thereto while keeping the temperature. Thereafter, 3,3,3-trifluoropropene (6.7 g, 70 mmol) was further added, followed by stirring for 5 to 10 minutes. The mixture was subjected to separation and distillation, thereby giving a composition containing $CF_3$—CHOH—$CH_2OH$ and trifluoroacetic acid with a conversion rate of 98.3%, selectivity of 80.3%, and yield of 78.9%. The total trifluoroacetic acid content of the composition was 2,500 ppm.

Example 2

Sodium periodate (22.5 g, 105 mmol) and water (30 mL) were stirred at 0° C. to 5° C., and ruthenium(III) chloride (71.5 mg, 0.35 mmol), ethyl acetate (100 mL), and acetonitrile (100 mL) were added thereto while keeping the temperature. Thereafter, concentrated sulfuric acid (1.4 g, 14 mmol) was added, and 3,3,3-trifluoropropene (6.7 g, 70 mmol) was further added, followed by stirring for 5 to 10 minutes. The mixture was subjected to separation and distillation, thereby giving a composition containing $CF_3$—CHOH—$CH_2OH$ and trifluoroacetic acid with a conversion rate of 97.2%, selectivity of 97.8%, and yield of 95.1%. The total trifluoroacetic acid content of the composition was 1,700 ppm.

Example 3

Sodium periodate (22.5 g, 105 mmol) and water (30 mL) were stirred at 0° C. to 5° C., and ruthenium(III) chloride (71.5 mg, 0.35 mmol), ethyl acetate (100 mL), and acetonitrile (100 mL) were added thereto while keeping the temperature. Thereafter, acrylonitrile (3.7 g, 70 mmol) was further added, followed by stirring for 5 to 10 minutes. The mixture was subjected to separation and distillation, thereby giving a composition containing NC—CHOH—$CH_2OH$ and cyanoformic acid with a conversion rate of 97.6%, selectivity of 82.3%, and yield of 80.3%. The total cyanoformic acid content of the composition was 3,500 ppm.

Comparative Example 1

Potassium ferricyanide (155 mmol), water (120 mL), t-butyl alcohol (120 mL), and potassium osmate dihydrate (261 mg, 0.71 mmol) were stirred at 0° C. to 5° C., and 3,3,3-trifluoropropene (6.7 g, 70 mmol) was added thereto, followed by stirring for about 17 hours. The mixture was subjected to extraction and distillation, thereby giving a composition containing $CF_3$—CHOH—$CH_2$OH and trifluoroacetic acid with a conversion rate of 40.2%, selectivity of 88.4%, and yield of 35.5%. The total trifluoroacetic acid content of the composition was 500 ppm.

The conversion rate in Examples 1 and 2 and Comparative Example 1 refers to the conversion rate of an olefin (for example, 3,3,3-trifluoropropene in Example 1) measured by $^{19}$F-NMR. The selectivity was measured by $^{19}$F-NMR. The product of the conversion rate and the selectivity was considered as the yield. Table 1 shows the results.

The conversion rate in Example 3 refers to the conversion rate of acrylonitrile measured by $^1$H-NMR. The selectivity was measured by $^1$H-NMR. The product of the conversion rate and the selectivity was considered as the yield. Table 2 shows the results.

TABLE 1

| | $^{19}$F-NMR area % (standard substance: $C_6F_6$, solvent: $CDCl_3$) | | | |
|---|---|---|---|---|
| | C=C | COOH | CHOH—$CH_2$OH | Yield % |
| Chemical shift | −67 ppm | −75 ppm | −84 ppm | |
| Example 1 | 1.7 | 0.25 | 86.7 | 78.9 |
| Example 2 | 2.2 | 0.17 | 95.1 | 95.1 |
| Comparative Example 1 | 67.8 | 0.05 | 32.3 | 35.5 |

TABLE 2

| | $^1$H-NMR area % (standard substance: tetramethylsilane, solvent: $CDCl_3$, $D_2O$) | | | |
|---|---|---|---|---|
| | C=C | COOH | CHOH—$CH_2$OH | Yield % |
| Chemical shift | 5.56, 6.01 ppm | 11 to 12 ppm | 4.65, 3.76 ppm | |
| Example 3 | 1.8 | 0.35 | 96.2 | 80.3 |

The invention claimed is:
1. A method for producing a diol in high yields, comprising
oxidizing an olefin represented by Formula (1):

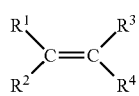

wherein $R^1$ is a group having an electronegativity of 3.3 to 5.0; and $R^2$ to $R^4$ are each independently a hydrogen atom, a cyano group, or an optionally substituted alkyl group, in the presence of a ruthenium compound to produce a diol represented by Formula (2):

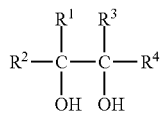

wherein $R^1$ to $R^4$ are as defined above.
2. The production method according to claim 1, wherein one of $R^2$ to $R^4$ is a hydrogen atom.
3. The production method according to claim 1, wherein two of $R^2$ to $R^4$ are hydrogen atoms.
4. The production method according to claim 1, wherein $R^2$ to $R^4$ are all hydrogen atoms.
5. The production method according to claim 1, further comprising collecting the ruthenium compound after the oxidization of the olefin.
6. A method for producing a diol in high yields, comprising
oxidizing an olefin represented by Formula (3):

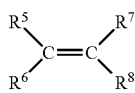

wherein $R^5$ is a cyano group or a fluorine-containing alkyl group; and $R^6$ to $R^8$ are each independently a hydrogen atom, a cyano group, or an optionally substituted alkyl group, in the presence of a ruthenium compound to produce a diol represented by Formula (4):

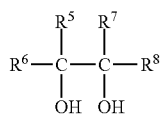

wherein $R^5$ to $R^8$ are as defined above.
7. The production method according to claim 6, wherein one of $R^6$ to $R^8$ is a hydrogen atom.
8. The production method according to claim 6, wherein two of $R^6$ to $R^8$ are hydrogen atoms.
9. The production method according to claim 6, wherein $R^6$ to $R^8$ are all hydrogen atoms.
10. The production method according to claim 6, further comprising collecting the ruthenium compound after the oxidization of the olefin.
11. A composition comprising:
a diol represented by Formula (4):

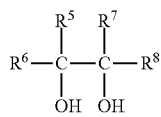

wherein $R^5$ is a cyano group or a fluorine-containing alkyl group; and $R^6$ to $R^8$ are each independently a hydrogen atom, a cyano group, or an optionally substituted alkyl group, and
an acid compound represented by Formula (5):

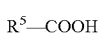

wherein $R^5$ is as defined above, the composition containing the acid compound in an amount of 1,000 to 10,000 ppm.

\* \* \* \* \*